US008529945B2

(12) United States Patent
Ajani et al.

(10) Patent No.: US 8,529,945 B2
(45) Date of Patent: *Sep. 10, 2013

(54) ORAL ANTIMICROBIAL PHARMACEUTICAL COMPOSITIONS

(75) Inventors: Mauro Ajani, Milan (IT); Roberta Bozzella, Milan (IT); Giuseppe Celasco, Genoa (IT); Roberto Villa, Lecco (IT)

(73) Assignee: Cosmo Technologies Ltd., Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/616,582

(22) Filed: Sep. 14, 2012

(65) Prior Publication Data

US 2013/0004569 A1    Jan. 3, 2013

Related U.S. Application Data

(63) Continuation of application No. 11/571,044, filed as application No. PCT/EP2005/052025 on May 3, 2005, now Pat. No. 8,486,446.

(30) Foreign Application Priority Data

Jun. 25, 2004   (IT) .............................. MI2004A1295

(51) Int. Cl.
    *A61K 9/52*   (2006.01)
(52) U.S. Cl.
    USPC ........................................................ 424/457
(58) Field of Classification Search
    USPC ........................................................ 424/457
    See application file for complete search history.

(56) References Cited

U.S. PATENT DOCUMENTS

| | | | | |
|---|---|---|---|---|
| 5,171,580 | A | * | 12/1992 | Iamartino et al. ............. 424/490 |
| 5,849,327 | A | | 12/1998 | Berliner et al. |
| 5,985,823 | A | | 11/1999 | Goldstein |
| 6,248,363 | B1 | | 6/2001 | Patel et al. |
| 7,410,651 | B2 | | 8/2008 | Villa et al. |
| 7,410,652 | B2 | | 8/2008 | Villa et al. |
| 7,431,943 | B1 | | 10/2008 | Villa et al. |

FOREIGN PATENT DOCUMENTS

| | | |
|---|---|---|
| EP | 0 366 621 | 5/1990 |
| EP | 0 572 942 | 12/1993 |
| EP | 0 793 959 | 9/1997 |
| EP | 1 183 014 | 3/2002 |
| EP | 1516620 | 3/2005 |
| GB | 2 245 492 | 1/1992 |
| GB | 2 352 172 | 1/2001 |
| WO | 90/04386 | 5/1990 |
| WO | WO-00/25756 | 5/2000 |
| WO | WO-00/76478 | 12/2000 |
| WO | WO-01/11077 | 2/2001 |
| WO | WO-2004/017962 | 3/2004 |
| WO | WO-2005/030173 | 4/2005 |

OTHER PUBLICATIONS

Tursi et al (Long-term treatment with mesalazine and rifaximin versus rifaximin alone for patients with recurrent attacks of acute diverticulitis of colon. Dig Liver Dis. Jul. 2002;34(7):510-5 (abstract only)).*

Merck (The Merck Index: An Encyclopedia of Chemicals, Drugs, and Biologicals edited by S. Budavari et al., Merck Research Laboratories, 1996, Whitehouse Station, N J, 12 ed., cover, title page, 1414-1415; see IDS).*

Faller, A. et al., "Anatomia e Fisiologia del Corpo Umano (anatomy and Physiology of the Human Body)," Edizione Italiana Riveduta ed Ampliate Sulia III Edizione Tedesca, vol. 1, Edizioni Minerva Medica, Turin, 1973, pp. 235-254, 12 pages.

Celasco, G. et al., "Efficacy of Intracolonic Administration of Low-Molecular-Weight Heparin CB-01-05, Compared to Other Low-Molecular-Weight Heparins and Unfractionated Heparin, in Experimentally Induced Colitis in Rat," Digestive Diseases and Sciences, 2008 vol. 53, pp. 3170-3175, 6 pages, copyright The Author(2) 2008.

Dotan, I. et al., "Heparin and Low-Molecular-Weight Heparin (Enoxaparin) Significant Ameliorate Experimental Coltis in Rats," Altmentary Pharmacology and Therapeutics, 2001, vol. 15,pp. 1687-1697, 11 pages, copyright 2001 Blackwell Science Ltd.

Di Stefano, A.F.D. et al., "Systemic Absorption of Rifamycin SV MMX Healthy Administered as Modified-Release Tablets in Healthy Volunteers," Antimicrobial Agents and Chemotherapy, May 2011, vol. 55, No. 5, pp. 2122-2128, 7 pages, copyright 2011 American Society for Microbiology.

Celasco, G. et al., "Clinical Trial: Oral Colon-Release Pamaparin Sodium Tablets (CB-01-05 MMX®) for Active Left-Sided Ulcerative Colitis,"Alimentary Pharmacology and Therapeutics, vol. 31, pp. 375-386, 12 pages, copyright 2010 Cosmo Research and Development.

Farrell, D. et al., "In Vitro Activity and Single-Step Mutational Analysis of Rifamycin SV Tested Against Enteropathogens Associated with Traveler's Diarrhea and Clostridium Diffcile," Antimicrobial Agents and Chemotherapy, March 2011, vol. 55, No. 3, pp. 992-996, 5 pages, copyright 2011, American Society for Microbiology.

Steward, P.A., "Review of Pharmaceutical Controlled Release Methods and Devices," Literature Review of Pharmaceutical Controlled Release Methods & Devices, 1995, 11 pages, http://www.initium.demon.co.uk/rel_nf.htm, Jul. 21, 2009.

Sánchez et al., Dyes and Pigments, vol. 37, No. 2, pp. 93-102 (1998).

Sorice, F. et al., "Intossicazioni alimentari e infezioni batteriche del tubo digerente,"Medicina Clinica. Edizioni Medico Scientifiche, Turin, 2002.

The Merck Index: An Encyclopedia of Chemicals, Drugs, and Biologicals edited by S. Budavari et al., Merck Research Laboratories, 1996, Whitehouse Station, NJ, 12 ed., cover, title page, 1414-1415.

CAS Registry entries fo rifaximin and rifamycin SV entered Nov. 16, 1984.

Amenta M., et al., Intestinal Protozoa in HIV-Infected Patients: Effect of Rifaximin in Cryptosporidium parvum and Blastocystis hominia infections, Journal of Chemotherapy, (1999); 11:391-395.

Beseghi U., et al., Comparison of two non-absorbable antibiotics for treatment of bacterial entaritis in childre, European Review for Medical and Pharmacological Sciences, (1998); 3-4:131-138.

DuPont H. L., et al., Rifaximin versus Ciprofloxacin for the Treatment of Traveler's Diarrhea: A Randomized, Double-Blind Clinical Trail, Clinical Infectious Diseases, (2001); 33:1807-1815.

(Continued)

*Primary Examiner* — Jake Vu
(74) *Attorney, Agent, or Firm* — Rothwell, Figg, Ernst & Manbeck, P.C.

(57) ABSTRACT

The present invention relates to oral pharmaceutical compositions with controlled and/or programmed release containing at least one active ingredient having antimicrobial and/or anti-infectious activity for the treatment of infections of the large intestine, in particular the colon.

27 Claims, No Drawings

(56) References Cited

OTHER PUBLICATIONS

DuPont H. L., et al., Rifaximin: A Nonabsorbed Antimicrobial in the Therapy of Travlers' Diarrhea, Digestion, (1998); 59:708-714.
English Abstract of Chinese Publication No. 1 398 587 A, Document No. , XP002337500, Feb. 26, 2003.
English Abstract of Chinese Publication No. 1 097 308 A, Document No. , XP002337501, Jan. 18, 1995.
Tracy, J.W. et al., "Metronidazole", *Goodman & Gilman's The Pharmacological Basis of Therapeutics*, Ninth Ed., McGraw Hill, 1996, pp. 995-998.
Braga, P.C., "Enteric microflora nd its regulation." *Drugs in Gastroanterology.*. Raven Press, New York, 1991, pp. 501-508.
Braga, P.C., "Interaction of antibiotics on enteric microblora." *Drugs in Gastroanterology*, Raven Press, New York, 1991, pp. 509-517.
Jackson, B.T., "Diverticular disease." *Inflammatory Bowel Diseases*. Chruchill Livingston, New York, 1997, pp. 443-447.
Sorice, F. et al., "Intossicazioni alimentari e infezioni del tubo digerente," *Medicina Clinica*. Edizioni Medico Scientifiche, Turin, 2002.
Wikipedia, the free encyclopedia, pages filed in corresponding Japanese case explaining the difference between rifamicyn sv and various other active ingredients, 22 pages, Jul. 21, 2011.
Quattrocchi, C. et al., "Rifamycin SV: Evaluation of the activity in DNB-induced colttis in rats and on IFNy production in ConA stimulated rat splenocytes," Rifa MMX 090127 ECCO poster, 1 page, Feb. 2009.

\* cited by examiner

ORAL ANTIMICROBIAL PHARMACEUTICAL COMPOSITIONS

CROSS REFERENCE TO RELATED APPLICATIONS

This application is a continuation of U.S. patent application Ser. No. 11/571,044, filed Feb. 5, 2007, which is a U.S. National Phase under 35 U.S.C. §371 of International Application No. PCT/EP2005/052025, filed May 3, 2005, which claims the benefit of Italian Patent Application MI2004 A 001295 filed on Jun. 25, 2004, all of which are incorporated by reference herein in their entirety.

DESCRIPTION

Intestinal infections are common diseases caused by the colonization of the intestine by foreign pathogenic agents of various origins, or caused by intestinal microorganisms that are normally present becoming virulent.

It is known that the intestine is divided into two distinct portions: the proximal portion, called the "small intestine", which is formed, in the craniocaudal direction, by the duodenum, the jejunum and the ileum, and the distal portion, called the "large intestine", which is formed by the colon and the recto-anus (Faller A, Scevola G. *Anatomia e Fisiologia del Corpo Umano* (*Anatomy and Physiology of the Human Body*). Vol I. Edizioni Minerva Medica, Turin, 1973, pp. 235-254).

The two portions, the small intestine and the large intestine, are completely separated anatomically by the ileocaecal valve which permits the passage of the intestinal contents from the small intestine to the large intestine but not vice versa. Besides from the anatomical-structural point of view, the large intestine is quite different from the small intestine also, and above all, from the functional point of view (Braga PC. *Enteric microflora and its regulation*. In *Drugs in Gastroenterology*. Raven Press, New York, 1991, pp. 501-508).

While the small intestine is assigned to the digestion of the majority of the food, to the absorption thereof, to the production of B-complex vitamins and vitamin K, to the metabolism of biliary acids and various other organic substances and to the rapid transfer of the alimentary bolus to the sections further downstream, the large intestine provides for the absorption of water, for the digestion of vegetable fibres and for the completion of some digestive processes initiated in the small intestine. In addition, the large intestine differs from the small intestine by the presence of an extremely rich bacterial flora, the balance of which is of fundamental importance in regulating the ambient pH, motility, the production of gas and ammonia, the formation of faeces, and the production of metabolites essential for maintaining the good functioning of the large intestine.

These many differences between the small intestine and the large intestine explain the distinctive nature of some pathologies which occur at the expense of the large intestine and in particular the colon.

The colon is the portion of the large intestine that is host to the majority of the bacterial strains and that offers conditions of pH, anaerobiosis, humidity and slowness of transit that are particularly suitable for the permanent flora potentially becoming virulent or for the proliferation of and colonization by pathogenic bacteria. For those reasons, the colon is the sector of the intestine most susceptible to infection; in fact, infections located in the colon (infectious colitis, bacillary dysentery, diarrhoea, pseudomembranous colitis, diverticulitis, etc.) constitute an important and autonomous chapter in the gastroenterological monograph (Sorice F., Vullo V. *Intossicazioni alimentari e infezioni del tubo digerente*. (*Food Poisoning and Infections of the Alimentary Canal*). In: *Medicina Clinica* (*Clinical Medicine*).Edizioni Medico Scientifiche, Turin, 2002).

In addition, the increased endoluminal pressure, linked with the production of gas and associated with predisposing local factors, can promote the occurrence of diverticula which are susceptible to infection and inflammation and which are located exclusively in the colon (Jackson BT. *Diverticular disease*. In: *Inflammatory Bowel Diseases* Churchill Livingston, New York, 1997, pp. 443-447).

Currently, the oral therapy of intestinal infections, and in particular colon infections, uses substances having antibacterial activity which must have specific characteristics such as: broad spectrum of activity on Gram+ and Gram- bacteria, resistance to strongly acidic environments, such as the gastric environment, anti-infectious activity independent of the presence of the intestinal biomass, residence inside the intestine for an appropriate period of time, good penetrability into the infecting host cell and good tolerability (Braga PC. *Interaction of antibiotics on enteric microflora*. In: *Drugs in Gastroenterology*. Raven Press, New York, 1991, pp. 509-517).

Therapy with antibacterial agents administered in the oral preparations employed today has at least two limitations. In the first place, the antibacterial agents, if not suitably protected, may lose their efficacy owing to the enzymatic or degradative inactivation which occurs during their passage through the stomach or through the small intestine.

In addition, the pharmaceutical forms nowadays used, although they permit the administration of the active ingredient in discrete doses, release it too rapidly in relation to the time taken to pass through the digestive tract, so that the active ingredient performs its anti-infectious activity in an indiscriminate manner along the entire gastro-intestinal tract.

This leads to the disappearance of the non-pathogenic bacterial flora living in the small intestine (duodenum, jejunum and the ileum), which flora, since it is not normally the seat of infection, should be protected and not subjected to the sterilizing action characteristic of the formulations used today.

For it is known that this bacterial flora is important in fundamental biological processes, such as, for example, the digestion and absorption of alimentary nutritive components, the production and absorption of vitamins (vitamin K and B-complex vitamins), the metabolism of biliary acids and of steroid hormones, the activation and inactivation of various substances, the protection of the organism from xenobiotics, (Braga PC. Ibidem).

In particular, the usual oral antibacterial therapies for the treatment of pathologies located in the colon have often given a contradictory result, probably owing to the excessive dilution of the active ingredients in the intestinal lumen; this dilution is caused by the premature release of the antimicrobial agent from the pharmaceutical form containing it, which takes place as early as in the stomach and in the immediate vicinity of the patient's pyloric valve.

In addition, although the antimicrobial agents used for the disinfection of the digestive tract often do not have a high rate of metabolism, in order to maintain unaltered the therapeutic possibility connected with the administration of a traditional form containing antimicrobial agents, no phenomenon of metabolic degradation should occur, in order to avoid any weakening of the therapeutic efficacy associated with the presence of the antimicrobial agent.

Therefore, in such cases, in order to ensure the real efficacy of the anti-infectious therapy, it is felt that there is a need for the possibility of a controlled and site-specific form of administration.

For the release of the antimicrobial/anti-infectious active ingredient in the immediate vicinity of the region where a diverticulum or a generic infection becomes established, leads to the formation of a much higher concentration gradient than in the case of a conventional form of oral administration, with the consequent greater possibility that the antimicrobial agent will succeed in penetrating to the inside of the diverticulum.

In that situation, particular importance is attached to the possibility of the remission also of infectious pathologies which are not widespread but which are of considerable socio-epidemiological importance, such as bacillary dysentery and pseudomembranous colitis, and also of infectious complications in surgical operations at the expense of the large intestine and in particular the colon.

Rifamicin SV, which has been known since the 1960s, is a semi-synthetic active ingredient which is derived from rifamicin S and which has a strong antimicrobial and/or anti-infectious activity both locally and parenterally. Its activity has also been evaluated in vitro at minimum concentrations (mcg/ml) on Gram+bacteria, such as *Staphylococcus aureus* or *Enterococcus faecalis*, as well as at higher concentrations on Gram- bacteria, such as *Escherichia coli, Salmonella, Enterobacter aerogenes, Enterobacter cloacae* or *Pseudomonas aeruginosa*.

Rifamicin SV, in the form of its sodium salt, is currently marketed under the name Rifocin® both for external topical use and for injection. In particular, the topical use, indicated for the local treatment of infectious processes, is limited to external use by means of a solution of the active ingredient which is to be diluted at the time of use.

Patent application WO01/11077, which is incorporated herein by reference, describes the use of antimicrobial agents, including the generic rifamicin, for the preparation of pharmaceutical compositions that can be used in the treatment of pathologies caused by anomalous bacterial growth (Small Intestine Overgrowth—SIBO) at the expense of the small intestine. Those compositions are formulated in such a manner as to release the active ingredient rapidly in the proximal portion of the intestine, that is to say, solely in the small intestine (duodenum, jejunum and ileum).

Metronidazole is a nitroimidazole chemotherapeutic agent having powerful antimicrobial activity and a broad spectrum of action both on Gram+ bacteria and Gram-bacteria. In addition, metronidazole is known to have a proven antiprotozoan activity (Tracy J. W. et al., *Metronidazole*, in: Goodmen & Gilman's, *The Pharmacological Bases of Therapeutics*, IX Ed., 1996, pp 995-998). Current therapy with metronidazole is supported with tablets (Flagyl®) that contain 250 mg of active ingredient and that are formulated for immediate release.

It has now surprisingly been found that the efficacy of antimicrobial/anti-infectious active ingredients, such as rifamicin SV and/or metronidazole, in the treatment of infections of the large intestine, and in particular of the colon, can be substantially potentiated thanks to the elimination of the undesired effects described above (avitaminosis, destruction of non-pathogenic bacterial flora, etc.) which are caused by the premature release of the active ingredients in the first portions of the digestive canal, such as the stomach, the duodenum and the jejunum, and thanks to the protection from the metabolic-enzymatic inactivation of the active ingredients which is brought about before the ingredients can reach the site of infection.

In particular, the efficacy of rifamicin SV was verified by means of an evaluation of the MIC (Minimum Inhibiting Concentration) on specific pathogenic bacterial strains, such as, for example, *Escherichia coli, Enterobacter faecalis, Proteus vulgaris, Pseudomonas aeruginosa, Salmonella typhi* and *Enterobacter cloacae* as shown in the following Table A.

TABLE A

| Bacterial species | MIC (mcg/ml) |
|---|---|
| *Escherichia coli* (ATCC 30218) | 400 |
| *Enterobacter faecalis* (ATCC 29212) | 25 |
| *Proteus vulgaris* (ATCC 13315) | 400 |
| *Pseudomonas aeruginosa* (ATCC 27853) | >400 |
| *Salmonella typhi* (ATCC 13331) | >400 |
| *Enterobacter cloacae* (ATCC 17446431) | >400 |
| *Staphylococcus aureus* (ATCC 25213) | <0.4 |

The present invention therefore relates to oral pharmaceutical compositions containing an active ingredient having antimicrobial/anti-infectious activity, such as rifamicin SV and/or metronidazole, characterized in that they are formulated in such a manner as to release the active substances substantially in the portion of the large intestine where their specific sterilizing action is required, but leaving unaltered the non-pathogenic bacterial flora present in the portions of the small intestine which are not affected by the infection.

In particular, the formulations according to the present invention are capable of releasing the active ingredient solely in the colon, thus ensuring localized and restricted anti-infectious efficacy.

Consequently, the advantage of the formulations of the invention is the particular site-specificity in the large intestine, and in particular in the colon, which permits a greater concentration of the active substance in the infected distal intestinal region with complete preservation of the healthy proximal regions.

This advantage is displayed mainly during the treatment of specific pathological situations in the colon region, such as infectious colitis, bacillary dysentery, diverticular disease and diverticulitis where the site-specificity and the tolerability of the formulations play a key role in the resolution of the pathology.

A further advantageous application of the formulations of the invention is their use during preparation for surgical operations on the large intestine, in ileocolic anastomoses, and in the sterilization of the ammonia-producing colonic flora in order to prevent and/or treat hyperammonaemias. In these last-mentioned cases, the site-specificity of treatment and the consequent concentration of the activity of the active ingredient may lead to a significant resolution of cases which would otherwise involve substantial complications.

In the formulations of the invention, the substances having antimicrobial/anti-infectious activity are contained in an amount of from 10 to 90% by weight; in particular rifamicin SV is contained in an amount of from 20% to 60% by weight, while metronidazole is contained in an amount of from 25% to 70% by weight. The oral formulations of the invention are selected from tablets, capsules, granules and/or microgranules.

A preferred embodiment of the present invention comprises a system for controlled release which is characterized by the presence of a first, amphiphilic, matrix in which the active ingredient is incorporated and which is in turn dispersed in a second, lipophilic, matrix. The form so obtained is again in turn dispersed in a third, hydrophilic, matrix before producing the final oral pharmaceutical form.

The lipophilic matrix of the present invention is represented by substances having a melting point lower than 90° C., such as, for example, beeswax, carnauba wax, stearic acid, stearin and the like; the amphiphilic matrix is represented by substances selected, for example, from phospholipids, ceramides, sphingomyelins, lecithins, alkyl block copolymers, salts of sulphated alkyl acids, polyoxyethylenated alkyl, derivatives of sorbitan and the like, while the hydrophilic matrix is represented by generally cross-linked or linear polymeric or copolymeric substances, which are known as hydrogels, that is to say, substances capable of increasing their mass and their weight, owing to the polar groups present in the main or side polymer chains, when they come into contact with molecules of water.

In particular, the hydrophilic matrix corresponds to substances selected, for example, from cellulose derivatives, such as hydroxyalkylcelluloses, alkylcelluloses, carboxyalkylcelluloses and their salts or derivatives, polyvinyl alcohols, carboxyvinyl derivatives, polysaccharide derivatives of anionic or cationic nature, such as, for example, hyduronic acid, glucuronic acid, or glucosamines, pectins and/or their derivatives.

In this preferred embodiment, the matrices are dispersed in one another in succession together with the active ingredient, thus bringing about the formation of a homogeneous structure responsible for the site-specificity of release.

In a further embodiment of the present invention, the tablets obtained are finally subjected to a coating process using gastroresistant substances, such as, for example, polymers of acrylic and methacrylic acids (Eudragit) and/or derivatives of cellulose phthalate.

Systems of controlled and/or programmed release suitable for the present invention are described in EP 1183014, GB 2245492 and EP572942, which are also incorporated herein by reference.

The following Examples describe the invention in detail without limiting the content thereof in any way.

EXAMPLE 1

200 g of rifamicin SV are mixed with 5 g of stearic acid, 7 g of carnauba wax, 8 g of sodium dioctyl sulphosuccinate, 100 g of lactose and 10 g of sodium edetate and granulated with a solution containing 25 g of low-viscosity polyvinylpyrrolidone in 0.2 liter of purified water. When the granulate has been dried, it is mixed with 100 g of sodium carboxymethylcellulose, 25 g of silica, 5 g of glycerol palmitostearate and 10 mg of talcum before being subjected to compression to the unit weight of 495 mg/tablet. The cores so obtained are then film-coated with a hydroalcoholic dispersion of acrylic and methacrylic acid esters, titanium dioxide, talcum and triethyl citrate, which confers on the product resistance to disintegration in a strongly acidic environment, simulating the environment of the stomach and the small intestine. The dissolution of the tablets is practically zero in pH conditions of less than 7 and is progressive in an enteric buffer at pH 7.2 with the following percentage quotas:
    less than 20% after 1 hour's residence,
    less than 50% after 3 hours' residence,
    more than 70% after 8 hours' residence.

EXAMPLE 2

500 g of rifamicin SV are mixed with 10 g of stearic acid, 10 g of beeswax, 10 g of sodium lauryl sulphate, 200 g of mannitol and 10 g of sodium edetate and granulated with a solution containing 50 g of hydroxypropylcellulose in 0.5 liter of water. When the granulate has been dried, it is mixed with 150 g of sodium hydroxypropylmethylcellulose, 25 g of silica, 5 g of glycerol palmitostearate and 10 mg of talcum before being subjected to compression to the unit weight of 490 mg/tablet. The cores so obtained are then film-coated with an aqueous dispersion of acrylic and methacrylic acid esters, iron oxide, talcum and triethyl citrate, with confers on the product resistance to disintegration in an acidic environment, simulating the environment of the stomach and the small intestine. The dissolution of the tablets is practically zero in pH conditions of less than 7 and is progressive in an enteric buffer at pH 7.2 with the following percentage quotas:
    less than 30% after 1 hour's residence,
    less than 60% after 3 hours' residence,
    more than 80% after 8 hours' residence.

EXAMPLE 3

2.5 kg of metronidazole are mixed with 70 g of stearic acid, 70 g of beeswax, 400 g of saccharose, 140 g of hydroxypropylmethylcellulose and 20 g of polysorbate and wet-granulated by the addition of purified water to a suitable consistency. The granulate is then dried and standardized in terms of dimensions before the addition of a further 200 g of hydroxymethylpropylcellulose, 600 g of microcrystalline cellulose, 30 g of glycerol palmitostearate and 70 g of silicon dioxide. After mixing, the powder is sent for compression to the unit weight of 450 mg/tablet.

The cores so obtained are then subjected to film-coating with a hydroalcoholic dispersion of acrylic and methacrylic acid esters, iron oxide, talcum and triethyl citrate, which confers on the product resistance to disintegration in an acidic environment. The dissolution of the tablets is practically zero in pH conditions of less than 7 and is progressive in an enteric buffer at pH 7.2 with the following percentage quotas:
    less than 25% within the first hour of residence,
    more than 25% and less than 70% within the third hour of residence,
    more than 80% after 8 hours' residence.

EXAMPLE 4

500 g of metronidazole are mixed with the components of the lipophilic/amphiphilic matrix, 5 g of stearic acid and 5 g of soya lecithin, some of the hydrophilic polymer, 100 g of hydroxypropylcellulose, and diluents, 150 g of mannitol.

The mixture is then made into a paste with a solution of low-viscosity hydroxypropylcellulose in purified water until a consistent granulate is obtained. After drying, the granulate obtained is mixed with a further 100 g of hydroxypropylcellulose, to which are added flow agents and lubricants, 5 g of silica, 5 g of talcum and 5 g of magnesium stearate, then compressed to a final weight of 925 mg/tablet. The tablets are finally coated with an alcohol-based suspension of acrylic and methacrylic copolymers capable of imparting to the tablets efficacious gastroresistance.

The rate of dissolution of those tablets is progressive and controlled, with approximately 20% of the active ingredient being released after the first hour of residence in enteric juice at pH 7.2, 50% after 2 hours and more than 80% after 4 hours, these figures being understood as quotas that are clearly subsequent to 2 hours' exposure at pH 1 and 1 hour's exposure at pH 6.4, reflecting the environment of the stomach and of the small intestine, respectively.

The invention claimed is:

1. A controlled release oral pharmaceutical composition comprising:
   (1) a tablet core comprising a homogeneous structure comprising (a) rifamycin SV in an amount effective for the treatment of an infection of the colon, (b) at least one lipophilic substance having a melting point less than about 90° C, (c) at least one amphiphilic substance and (d) at least one hydrophilic substance; and
   (2) a coating on said tablet core, said coating comprising a gastro-resistant substance, wherein said controlled release oral pharmaceutical composition releases said rifamycin SV substantially in the large intestine.

2. The controlled release oral pharmaceutical composition of claim 1, wherein said controlled release oral pharmaceutical composition releases said rifamycin SV solely in the colon.

3. The controlled release oral pharmaceutical composition of claim 1, wherein said rifamycin SV comprises rifamycin SV or a pharmaceutically acceptable salt thereof.

4. The controlled release oral pharmaceutical composition of claim 1, wherein said controlled release oral pharmaceutical composition is resistant to dissolution for 2 hours in an environment at pH 1.

5. The controlled release oral pharmaceutical composition of claim 1, wherein said controlled release oral pharmaceutical composition is resistant to dissolution for 1 hour in an environment at pH 6.4.

6. The controlled release oral pharmaceutical composition of claim 1, wherein said controlled release oral pharmaceutical composition is resistant to dissolution for 2 hours in an environment at pH 1 and is resistant to dissolution for 1 hour in an environment at pH 6.4.

7. The controlled release oral pharmaceutical composition of claim 1, wherein said gastro-resistant substance comprises at least one methacrylic acid polymer.

8. The controlled release oral pharmaceutical composition of claim 1, wherein said rifamycin SV comprises from about 20% to about 60% by weight of the total weight of said controlled release oral pharmaceutical composition.

9. The controlled release oral pharmaceutical composition of claim 1, wherein said infection of the colon is caused by gram negative bacteria, gram positive bacteria, or a combination of gram negative bacteria and gram positive bacteria.

10. The controlled release oral pharmaceutical composition of claim 1, wherein said infection of the colon is infectious colitis, bacillary dysentery, colitis, or diverticulitis.

11. The controlled release oral pharmaceutical composition of claim 1, wherein said infection of the colon causes diarrhea.

12. The controlled release oral pharmaceutical composition of claim 1, wherein said infection of the colon causes hyperammonaemia.

13. The controlled release oral pharmaceutical composition of claim 1, wherein said hydrophilic substance comprises at least one of a hydroxyalkylcellulose, an alkylcellulose, a carboxyalkylcellulose, a polyvinyl alcohol, a carboxyvinyl polymer, a carboxyvinyl copolymer, a polysaccharide, hyduronic acid, glucoronic acid, a glucosamine, or a pectin.

14. The controlled release oral pharmaceutical composition of claim 1, wherein said amphiphilic substance comprises at least one of a phospholipid, a ceramide, a sphingomyelin, lecithin, an alkyl block copolymer, a salt of a sulphated alkyl acid, a polyoxyethylenealkyl, or sorbitan.

15. The controlled release oral pharmaceutical. composition of claim 14, wherein said amphiphilic substance is lecithin.

16. The controlled release oral pharmaceutical composition of claim 1, wherein said lipophilic substance comprises at least one of beeswax, carnuba wax, stearic acid, or stearin.

17. A controlled release oral pharmaceutical composition according to claim 1, wherein said lipophilic substance comprises from about 1% to about 3.4% by weight of the total weight of the controlled release oral pharmaceutical composition.

18. The controlled release oral pharmaceutical composition of claim 1, wherein said hydrophilic substance comprises from about 8.4% to about 23% by weight of the total weight of the controlled release oral pharmaceutical composition.

19. The controlled release oral pharmaceutical composition of claim 1, wherein said rifamycin SV is in the form of a sodium salt.

20. The controlled release oral pharmaceutical composition of claim 19, wherein said sodium salt of rifamycin SV comprises from about 20% to about 60% by weight of the total weight of said controlled release oral pharmaceutical composition.

21. The controlled release oral pharmaceutical composition of claim 13, wherein said amphiphilic substance comprises at least one of a phospholipid, a ceramide, a sphingomyelin, lecithin, an alkyl block copolymer, a salt of a sulphated alkyl acid, a polyoxyethylenealkyl, or sorbitan.

22. The controlled release oral pharmaceutical composition of claim 21, wherein said amphiphilic substance is lecithin.

23. The controlled release oral pharmaceutical composition of claim 13, wherein said lipophilic substance comprises at least one of beeswax, carnuba wax, stearic acid, or stearin.

24. The controlled release oral pharmaceutical composition of claim 21, wherein said lipophilic substance comprises at least one of beeswax, carnuba wax, stearic acid, or stearin.

25. The controlled release oral pharmaceutical composition of claim 22, wherein said lipophilic substance comprises at least one of beeswax, carnuba wax, stearic acid, or stearin.

26. The controlled release oral pharmaceutical composition of claim 24, wherein said gastro-resistant substance comprises at least one methacrylic acid polymer.

27. The controlled release oral pharmaceutical composition of claim 25, wherein said gastro-resistant substance comprises at least one methacrylic acid polymer.

* * * * *

UNITED STATES PATENT AND TRADEMARK OFFICE
CERTIFICATE OF CORRECTION

PATENT NO.      : 8,529,945 B2
APPLICATION NO. : 13/616582
DATED           : September 10, 2013
INVENTOR(S)     : Mauro Ajani et al.

It is certified that error appears in the above-identified patent and that said Letters Patent is hereby corrected as shown below:

In the Specification

Col. 3, line 21: "Rifamicin" should be -- Rifamycin --

Col. 3, line 23: "rifamicin" should be -- rifamycin --

Col. 3, line 31: "Rifamicin" should be -- Rifamycin --

Col. 3, line 40: "rifamicin" should be -- rifamycin --

Col. 3, line 60: "rifamicin" should be -- rifamycin --

Col. 4, line 4: "rifamicin" should be -- rifamycin --

Col. 4, line 24: "rifamicin" should be -- rifamycin --

Col. 4, line 58: "rifamicin" should be -- rifamycin --

Col. 5, line 43: "rifamicin" should be -- rifamycin --

Col. 5, line 66: "rifamicin" should be -- rifamycin --

Signed and Sealed this
Twelfth Day of May, 2015

Michelle K. Lee
*Director of the United States Patent and Trademark Office*